United States Patent [19]

Shahani et al.

[11] 4,279,998

[45] Jul. 21, 1981

[54] REGENERABLE INSOLUBLE SUPPORT FOR PROTEIN IMMOBILIZATION

[75] Inventors: Khemchand M. Shahani, Lincoln; Frederick W. Wagner, Walton, both of Nebr.; Arun Kilara, State College, Pa.

[73] Assignee: The Board of Regents of the University of Nebraska, Lincoln, Nebr.

[21] Appl. No.: 47,727

[22] Filed: Jun. 12, 1979

Related U.S. Application Data

[63] Continuation-in-part of Ser. No. 697,240, Jun. 17, 1976, abandoned.

[51] Int. Cl.³ .................... C12N 11/00; C12N 11/16; C12N 11/10; C12N 11/06
[52] U.S. Cl. .............................. 435/174; 252/411 R; 260/141; 426/34; 435/178; 435/181
[58] Field of Search ............... 435/174, 177, 178, 179, 435/180, 181; 435/174, 177, 178, 179, 180, 181; 260/141; 252/411 R; 426/34

[56] References Cited

U.S. PATENT DOCUMENTS 4,043,869   8/1977   Barker et al. ................. 435/181 X

OTHER PUBLICATIONS

Cuatrecasas, et al., Adsorbents For Affinity Chromatography, Biochemistry, vol. 11, No. 12, 1972 (pp. 2291-2298).
Cuatrecasas, et al., Affinity Chromatography, Methods of Enzymology, vol. XXII, 1971 (pp. 345-379).
Cuatrecasas, P., Protein Purification By Affinity Chromatography, J. Biol. Chem., vol. 245, No. 12, 1970 (pp. 3059-3065).
Woychik et al., Preparation and Application of Immobilized B—Galactosidase of *Saccharomyces Lactis* Immobilized Enzymes in Food and Microbial Processes, Plenum Press, N.Y., 1974 (pp. 41-49).

*Primary Examiner*—David M. Naff
*Attorney, Agent, or Firm*—Vincent L. Carney

[57] ABSTRACT

To permit regeneration of an insoluble support for immobilized proteins, the protein is connected to the support by a spacer arm containing a diazo linkage and when the protein is denatured, the spacer arm is broken by reducing the diazo linkage to remove the denatured protein. New native protein of the same or of a different type is joined to the arm to permit reuse of the support. A preferred support containing a spacer arm is p-(N-acetyl-L-tyrosine azo)benzamidoethyl agarose. A protein is coupled to the carboxyl group of N-acetyl-L-tyrosine and when the protein is spent, the azo bond is reduced to remove the protein and leave p-aminobenzamido agarose which is diazotized and recoupled to N-acetyl-L-tyrosine which is then coupled to fresh protein.

12 Claims, No Drawings

REGENERABLE INSOLUBLE SUPPORT FOR PROTEIN IMMOBILIZATION

This application is a continuation-in-part of application Ser. No. 697,240 filed June 17, 1976, now abandoned, for ENZYME IMMOBILIZATION in the name of Khemchand Mottumal Shahani, Arun Kilara, and Frederick William Wagner.

This invention relates to regenerable insoluble supports for proteins and to processes by which the support materials may be regenerated by removing the spent proteins and attaching new proteins.

It is known to immobilize proteins on an insoluble support so as to be able to react the proteins with liquids flowing through the insoluble support. A process is disclosed for attaching the proteins to the insoluble support by a hydrocarbon arm inter alia by Pedro Cuatrecasas and Indu Parikh, *Biochemistry*, Vol. 11, pp. 2291 (1972). It is also known from U.S. Pat. No. 4,043,869 to Barker to absorb the azo diazotized M-diaminobenzene on to the surface of the support and attach the proteins to that surface. The proteins may be removed by treating the support with sodium dithionite to regenerate amino groups, diazotizing the amino groups again and attaching new biologically active protein molecules.

The method of providing a regenerative arm disclosed in the patent to Barker affects the activity of at least some of the protein molecules attached to it. The aromatic diamine will react with the tyrosine groups of some of the proteins and connect to multiple points, thus shifting the optimum pH.

Accordingly, it is an object of the invention to provide a novel insoluble support for proteins.

It is a further object of the invention to provide a support for the attachment of proteins which may be regenerated.

It is a still further object of the invention to provide a solid support for the connection of proteins by a spacer arm, which spacer arm may be broken and regenerated for the attachment of new protein.

In accordance with the above and further objects of the invention, a protein is immobilized in its stable state by activating a solid matrix, such as agarose, and connecting the protein through a hydrocarbon chain (sometimes referred to as a spacer arm) which includes diazo group. The protein is connected to the hydrocarbon chain at a single group and the hydrocarbon arm is sufficiently long to space the protein from the matrix so as to reduce the effect of the matrix on its activity. The diazo linkage can be broken when the protein is spent to remove the protein. The chain may be rebuilt and new protein attached after the removal of the old protein.

To attach the hydrocarbon spacer-arms the matrix may be advantageously activated by a cyanogen bromide activation technique for coupling to hydrocarbon arms which include an amino group. The hydrocarbon arm is, in turn, coupled to the protein preferentially at the α-amino group with a covalent bond.

The technique for preparing the reactant is similar to the technique used to prepare matrices in the prior art. This technique is disclosed in "Protein Purification by Affinity Chromatography", *The Journal of Biological Chemistry*, Vol. 245, No. 12, Issue of June 25, pp. 3059–3065, 1970 by Pedro Cuatrecasas and "Adsorbents for Affinity Chromatography". "Use of N-hydroxysuccinimide esters of agarose", *Biochemistry*, Vol. 11, No. 12, 1972, pp. 2291–2298 by Pedro Cuatrecasas and Indu Parikh. A similar approach is also disclosed in U.S. Pat. No. 3,167,485 to bond modified reusable enzymes to water insoluble carriers, but which results in random point coupling of the enzymes.

This matrix support has the advantages of not affecting the activity of the proteins attached to it and being regeneratable and therefore capable of less expensive operation.

Broadly, the invention contemplates a solid insoluble support from which proteins may be coupled and from which one protein can be removed and another substituted repeatedly. The proteins are coupled to the insoluble support by a hydrocarbon spacer arm principally to the α-amino groups, thus minimizing the number of points of chemical attachment. The immobilized proteins have a variety of uses in the art such as in affinity chromatography or in reactors for treating substrates with a enzyme. The manner of using such supports in proteins in affinity chromatography is documented in the references above and the use of such reactors in enzymes is the subject of the aforementioned application of which this application is a continuation-in-part.

The proteins are bonded to the carrier by an arm, generally a hydrocarbon arm, through covalent bonding to a group remote from the active site of the protein. Preferably, a single arm bonds the molecule of the protein at a single selected point and the molecule is sufficiently remote from the carrier so its activity is substantially unaffected by the carrier. It must be a minimum distance of approximately 5 angstrom units to accommodate the small arm that can couple the protein to a selected group and should be a maximum distance of 15 angstrom units to avoid unintentional separation of the coupled protein by shear forces during use.

Some types of substrates which benefit particularly from the use of the spacer arm are milk and sweet whey since they may be treated with a relatively inexpensive enzyme *Saccharomyces lactis* lactase at a pH of substantially 7, which is the optimum for several of such types of enzymes. Other substrates however benefit from the retention of activity through the use of the spacer arm, while the regeneration reduces the cost of the process.

The attachment is by a hydrocarbon arm which forms a covalent bond with only one reactive functional group of the protein under a predetermined set of chemical conditions, preferably to an α-amino group of the protein. This causes the protein to be linked at only one point, and the protein is selected so that this linkage at one point does not affect the activity of the protein, thus maintaining its normal pH activity profile. The arm is capable of being broken to remove spent protein and being rebuilt to receive new protein. For this purpose the arm advantageously includes a diazo linkage.

The section of the arm adjacent to the diazo bond must include a phenolic or aromatic compound with a carboxylic acid function for the selective attachment of proteins primarily to α-amino groups of the proteins. There are many such suitable compounds but N-acetyl-L-tyrosine is particularly advantageous because it is inexpensive and readily available so that its loss upon reducing the diazo bond to an azo compound is of no economic consequence.

In preparing the immobilized protein initially, a method is used which includes the steps of: (1) activating the matrix which may be agarose, dextran, polystyrene, porous glass or the like; (2) attaching the hydrocarbon arm with a diazo linkage in it; (3) activating the hydrocarbon arm; and (4) attaching the protein.

After the protein has been spent during use, the support may be renewed by a method which includes the further steps of: (5) removing the spent protein by reducing the diazo linkage; (6) rebuilding the hydrocarbon arm with the diazo linkage; (7) activating the hydrocarbon arm; and (8) attaching a new protein. These steps are shown in equations 1-8 in which the matrix is represented by a wavy line, the protein by RNH$_2$ and N,N'dicyclohexyl carbodiimide by DCC.

In this reaction, the matrix is reacted with cyanogen bromide plus a hydrocarbon having an amino group on both ends. The amino group at one end is intended for attachment to the matrix and the amino group at the other end is intended to lead eventually to the attachment of the protein. The use of the hydrocarbon arm, in a known manner, to couple the protein under controlled chemical conditions causes the attachment to be to the α-amino group of the protein rather than to the ε-amino group of the protein, thus removing it further from the active site of the protein. One of the coupling conditions generally includes a reaction at a neutral pH.

The method of activation is referred to in the field as cyanogen bromide activation. It is most commonly used for the activation of agarose (such as that sold under the tradename (Sepharose) and for the activation of cellulose. Other methods are known in the art. Of course, a combination of other reactions may be used as well. For example, agarose may be activated with cyanogen bromide and the protein can be attached either through the carbodiimide procedure or through diazotization.

When an inorganic carrier is used with some coupling techniques, the carrier is first prepared by silanization, but this step is not necessary if the cyanogen bromide process is used for coupling. Silanization consists of treatment with an organo-functional silane. For example, S-τ-amino propyl triethoxy silane may be used in this reaction. In this case the silane reacts with the available silanol or oxide groups on the carrier leaving the functional group available for coupling. The amino derivative thus generated can be covalently coupled to proteins by a wide variety of methods.

EXAMPLE 1

Agarose Beads—*Saccharomyces lactis* lactase

Firstly, agarose beads are activated as follows: 100 milliliters (packed volume) of well washed decanted Sepharose-4B (agarose beads) are mixed with 100 milliliters of water in a well ventilated hood and 20 grams of finely divided cyanogen bromide are added at once to the stirred suspension.

The pH of the suspension is immediately raised to and maintained at 11 with NaOH, the molarity of the NaOH being approximately 8. During the process, the temperature is maintained at about 20° C. by adding pieces of ice as needed. The reaction is complete in 8-12 minutes.

Once the reaction is complete, as indicated by the cessation of proton release, a large amount of ice is rapidly added to the suspension which is transferred quickly to a Buchner funnel (coarse disc) and washed under suction with a cold buffer. The buffer should be the same as that which is to be used in the coupling stage and the volume of the wash should be approximately one liter to one and one-half liters.

Secondly, an arm is coupled to the activated agarose as beads as follows: 100 milliliters of a solution including 13.8 milliliters of ethylenediamine is added to 100 milliliters of buffer and the combination is added to the moist washed Sepharose. The suspension is immediately mixed (in the Buchner funnel) with 6 N HCl at pH 10.0 with a glass stirring rod. The entire procedure of washing, adding the ligand solution, and mixing should consume less than 90 seconds.

The suspension is transferred from the Buchner funnel to a beaker containing a magnetic mixing bar and is gently stirred at 4° C. The stirring is continued for 16 to 20 hours at 4° Celsius. The substituted Sepharose is then washed with large volumes of water and the appropriate buffers until it is established with certainty that the ethylenediamine is no longer being removed.

Thirdly, the aminoethyl-Sepharose formed by the process is then added to an equal volume of 0.07 M p-nitrobenzoylazide in a 40% dimethyl formamide. An amount of 0.2 M sodium borate buffer is added to create a pH of 9.3 at room temperature. The mixture is allowed to stand at room temperature for one hour. The product of the above reaction is thoroughly washed with a 50% dimethyl formamide solution in the same buffer and then with 0.2 M sodium borate having a pH of 8.5. The p-nitrobenzoylazide used in the above reaction is prepared by slowly adding 0.7 grams of sodium azide dissolved in 2 milliliters of ice cold water to an ice cold solution of p-nitrobenzoylchloride (2.5 grams and 25 milliliters of acetone). The reaction is kept below 4° Celsius by incubating the reaction solution in a melting ice bath for 15 minutes. The resulting p-nitrobenzoylazide is obtained by adding 50 milliliters of cold distilled water to the reaction mixture, filtering and washing with still further water. The product is then dried over P$_2$O$_5$.

---

Agarose Matrix (1) 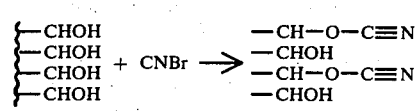 + CNBr → 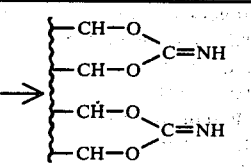 →

(2) 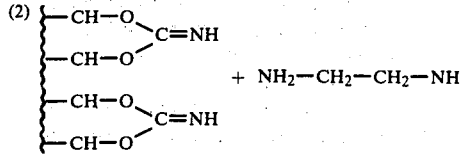 + NH$_2$—CH$_2$—CH$_2$—NH$_2$ → 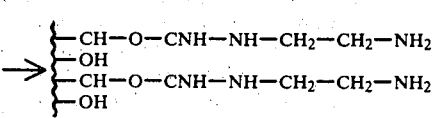

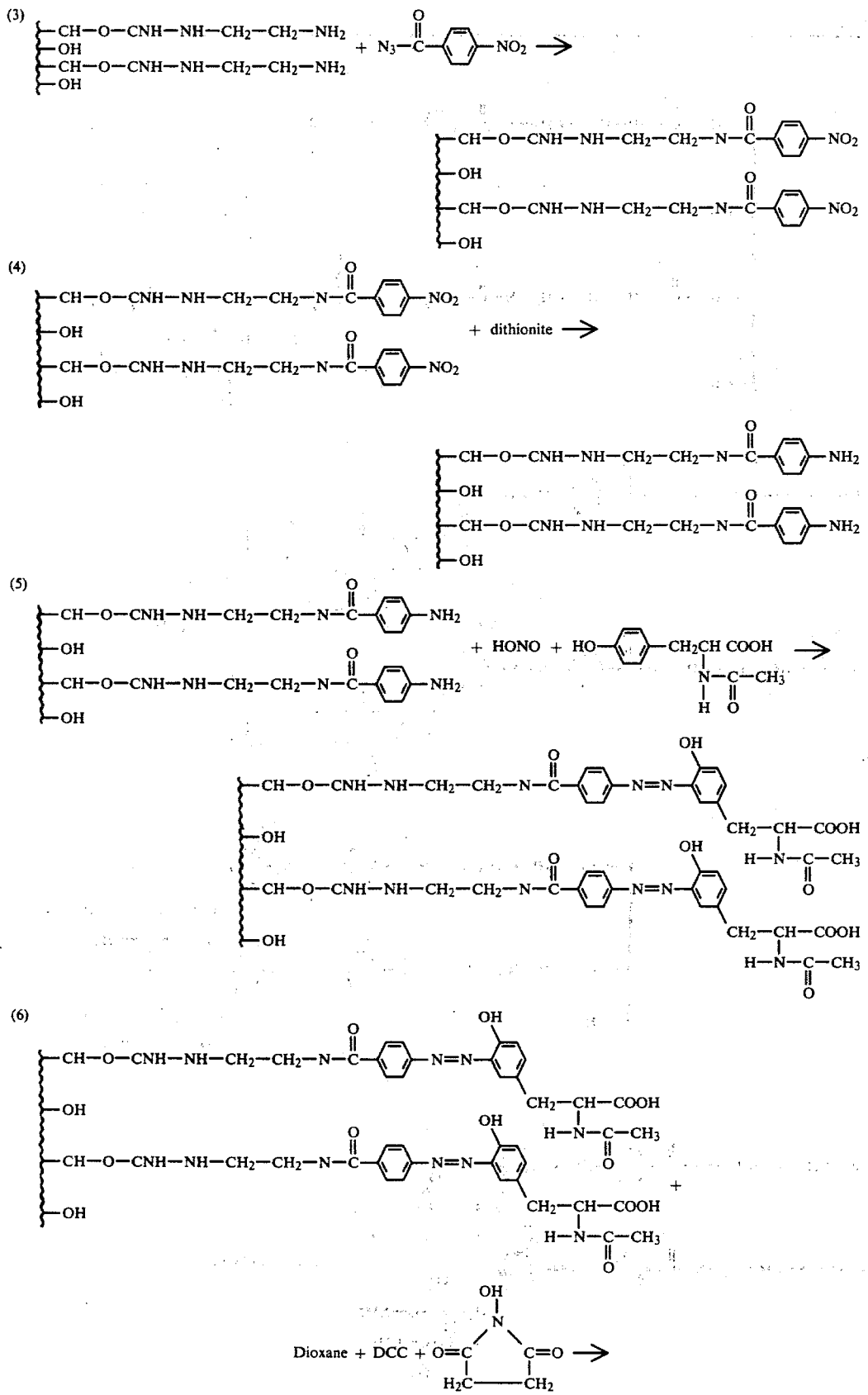

-continued
Agarose Matrix
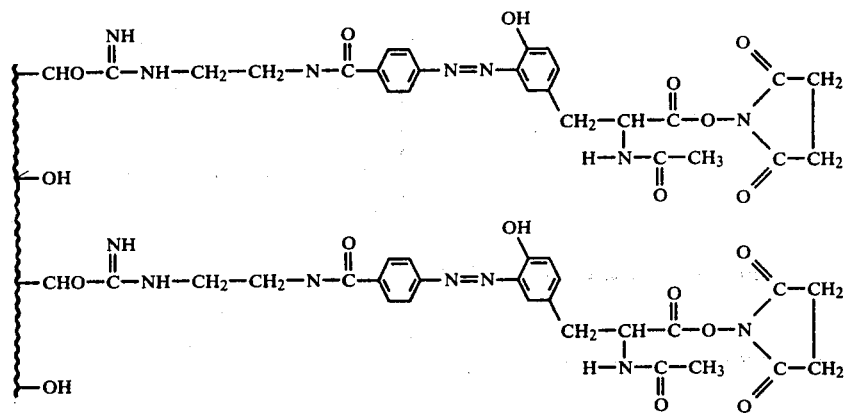
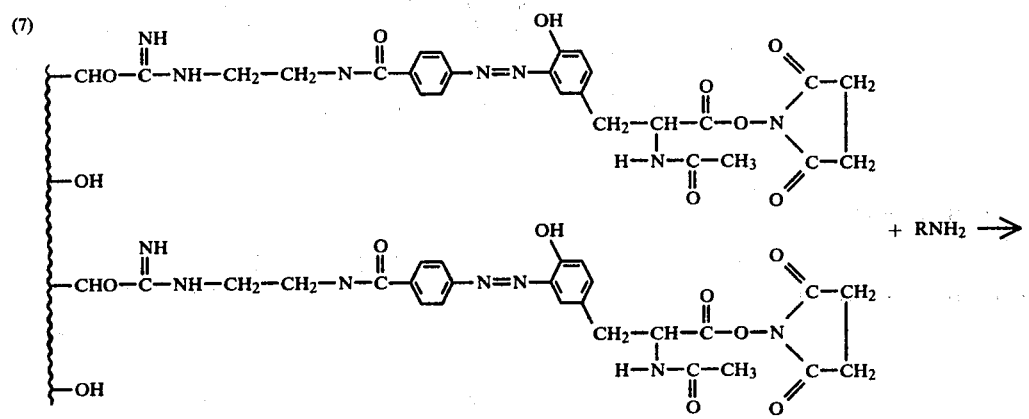
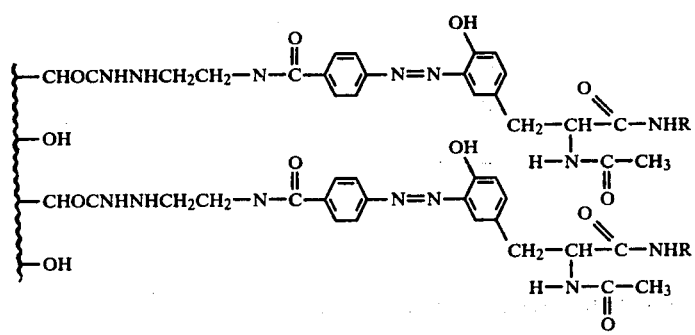
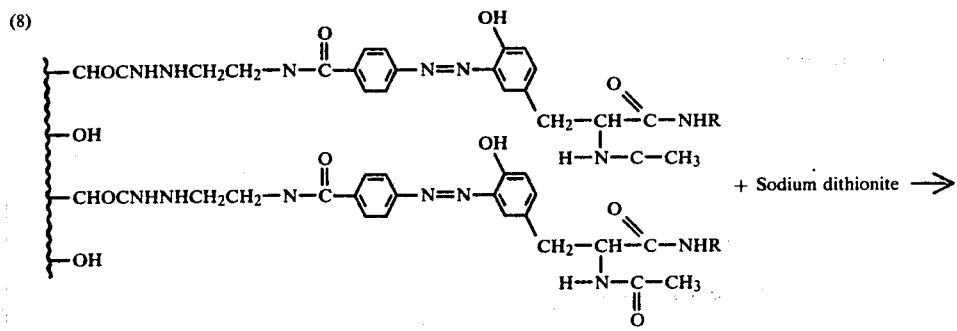

Agarose Matrix

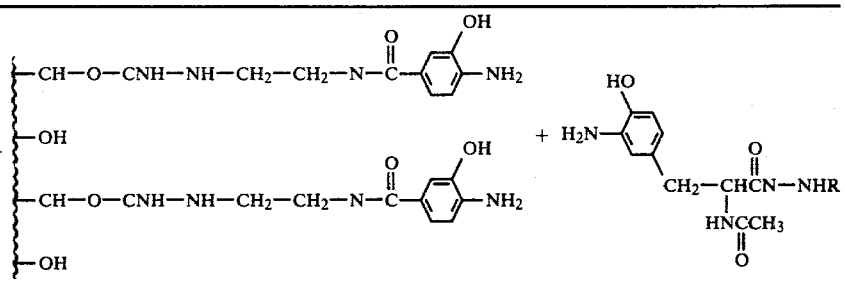

Fourthly, after this washing, the product is incubated in a 0.1 M sodium dithionite in a 0.2 M sodium borate solution for one hour to reduce the p-nitrobenzamidoethyl Sepharose. These reactions are illustrated in equations 1-4.

Fifthly, one hundred and fifty milliliters of the resulting gel of p-aminobenzamidoethyl is suspended in 250 milliliters of 0.1 N HCl and chilled to 4° C. A 1.4 grams solution of $NaNO_2$ is added and diazotization is allowed to proceed for 7 minutes. The diazotized resin is filtered and washed with a cold 0.1 N HCl solution. The resulting filter cake is slowly added to 150 milliliters of 0.1 M $NaHCO_3$ solution having a pH of 9.3 and containing 10 micromoles of N-acetyl-L-tyrosine. The resulting azo coupling reaction is allowed to proceed for 3 hours at room temperature. The reaction is complete when the resin assumes a deep red color. The reaction product is washed with water and then washed with dioxane and stored at room temperature in dioxane until used. This product is p-(N-acetyl-L-tyrosine azo) benzamidoethyl Sepharose.

Steps 1 through 5 result in the regenerable reactor base to which proteins may be coupled. Reduction of this base results in p-aminobenzamidoethyl agarose, which is the starting material shown in equation 5.

Sixthly, the reactor is activated before coupling the Saccharomyces lactis lactase lactase to it. To activate the reactor, it is suspended in dioxane to obtain a total volume equal to three times the volume of the packed gel. Solid N-hydroxysuccinimide is added and the suspension is stirred in a magnetic mixer to maintain a concentration of 0.1 molar.

Solid N,N'dicyclohexyl carbodiimide is added to adjust its concentration to 0.1 molar and the suspension is stirred gently for 7 minutes at room temperature. The activated product is washed over a Buchner funnel with 6 or 8 volumes of dioxane over a 10-minute period followed by 3 or 4 volumes of methanol (added by stirring with a glass rod) over 5 minutes to remove all of the precipitated dicyclohexylurea. This is followed by further washing (3 volumes) with dioxane. After drying the gel thoroughly under suction, the slightly moist cake of activated product is used immediately in the coupling reaction. This reaction is shown in equation 6.

Seventhly, Saccharomyces lactis lactase is coupled to the activated hydrocarbon arm as follows: the slightly moist cake of agarose is weighed and added to a rapidly stirred buffered solution maintained in an ice bath which contains 40 milligrams Saccharomyces lactis lactase per milliliter to be coupled. Generally, one gram of the gel is added for each 5 milliliters of ice cold solution. The pH of this solution is maintained at 7.0 and the temperature at 4° C. for approximately 6 hours. The gel is then washed to remove all unbonded lactase, after which glycine is added to achieve a concentration of 1 molar and the reaction is permitted to continue at room temperature for 2 hours. The activation and coupling steps are illustrated in equations 6 and 7.

The lactase substituted agarose is used as the reactor through which milk is circulated. After use for several days, the enzyme is replaced as follows:

The substituted agarose is washed. An 8 milliliter solution of 0.1 M sodium dithionite in 0.2 M $NAHCO_2$ at a pH between 8.5-9.0 is added at 20° C. The reaction is completed in about 2 hours after which time the agarose is washed until no further enzyme is being removed. The agarose can be reused by reduction of the diazo bond and repeating the steps of 5 through 7.

Eighthly, to reduce the diazo bond, the insoluble matrix with the attached protein is washed at room temperature with 10 volumes of 0.1 sodium dithionite in 0.2 M sodium borate buffer at a pH of 9.0 to remove the spent protein. The color due to the diazo bond disappears after about 5 volumes of buffer passes through the resin. The column is then washed with distilled water to remove excess sodium dithionite. The breaking of the diazo bond releases the protein together with the p-(N-acetyl-L-tyrosine) leaving benzamidoethyl agarose beads as illustrated in equation 8.

The benzamidoethyl agarose beads can then be reacted with nitrous acid and with p-(N-acetyl-L-tyrosine) at a pH of 9.5 as shown in equation 5 (step 5) to regenerate the solid support so that it is ready to receive a new protein. A new protein may be added as described in steps 6 and 7.

EXAMPLE 2 p-(N-acetyl-L-tyrosine azo) benzamidoethyl agarose beads with papian

Activated p-(N-acetyl-L-tyrosine azo) benzamidoethyl agarose beads were prepared as described in steps 1 through 6 of Example 1.

The moist cake of agarose was then weighed and added to a rapidly stirred solution maintained in an ice bath which contained the papian lactase to be coupled and a potassium phosphate buffer at a pH of 7.0 which contained 40 milligrams of the papian per milliliter of packed agarose cake. Generally, one gram of the cake was added for each 5 milliliters of ice cold solution. The reaction was allowed to proceed for 16 hours at 4° C. and then terminated by adding glycine to achieve a 0.2 molar solution. The product was then washed extensively with cold 0.1 M phosphate buffer at a pH 7 until all surface absorbed papian was eluted.

The insoluble support was regenerated and the spent enzyme removed after use by step 8 of example 1.

EXAMPLE 3 p-(N-acetyl-L-tyrosine azo) benzamidoethyl agarose beads with lipase

Activated p-(N-acetyl-L-tyrosine azo) benzamidoethyl agarose beads were prepared as described in steps 1 through 6 of Example 1.

The moist cake of agarose was then weighed and added to a rapidly stirred solution maintained in an ice bath which contained lipase to be coupled and a potassium phosphate buffer at a pH of 7.0 which contained 40 milligrams of the lipase per milliliter of packed agarose cake. Generally, one gram of the cake was added for each 5 milliliters of ice cold solution. The reaction was allowed to proceed for 16 hours at 4° C. and then terminated by adding glycine to achieve a 0.2 molar solution. The product was then washed extensively with cold 0.1 M phosphate buffer at a pH 7 until all surface absorbed lipase was eluted.

The insoluble support was regenerated and the spent enzyme removed after use by step 8 of Example 1.

EXAMPLE 4 p-(N-acetyl-L-tyrosine azo) benzamidoethyl agarose beads with beef heart mitochondrial ATPase Activated p-(N-acetyl-L-tyrosine azo) benzamidoethyl agarose beads were prepared as described in steps 1 through 6 of Example 1.

The moist cake of agarose was then weighed and added to a rapidly stirred solution maintained in an ice bath which contained the beef heart mitochondrial ATPase to be coupled and a potassium phosphate buffer at a pH of 7.0 which contained 40 milligrams of the beef heart mitochondrial ATPase per milliliter of packed agarose cake. Generally, one gram of the cake was added for each 5 milliliters of ice cold solution. The reaction was allowed to proceed for 16 hours at 4° C. and then terminated by adding glycine to achieve a 0.2 molar solution. The product was then washed extensively with cold 0.1 M phosphate buffer at a pH 7 until all surface absorbed beef heart mitochondrial ATPase was eluted.

The insoluble support was regenerated and the spent enzyme removed after use by step 8 above.

EXAMPLE 5

Polystyrene diazo bond—lactase coupled

Firstly, commercial 1 or 2 percent chloromethylated polystyrene is activated as follows: 100 milliliters of 1 or 2 percent chloromethylated polystyrene is saturated with a solution of tertiary butyloxycarbonyl glycine for one-half hour. A 4.7 millimeter solution is used.

The resulting product, which is tertiary butyloxycarbonylglymethyl polystyrene is soaked in 1 molar hydrochloric acid in acetic acid at 25° C. for 1 hour. The product of this reaction is glyclymethylpolystyrene.

The glyclymethylpolystyrene is processed as in steps 3 through 8 of Example 1.

EXAMPLE 6

Agarose beads—C-L-Valine Methyl Ester—Carbodiimide activation

Steps 1 through 5 are followed as in Example 1. For activation (step 6) three mills of the packed gel prepared in those steps is suspended in 9 milliliters of distilled water. Nineteen one-hundredths grams of 1-ethyl-3-(dimethylaminopropyl) carbodiimide is added and the pH is adjusted to 5.0. Thirty micromoles of the $^{14}$C-L-Valine methyl ester in 10 micromoles per milliliter of packed gel are added and the reaction allowed to proceed for 90 minutes at room temperature. After the reaction, the resin is washed in distilled water as the aliquots of the packed gel are dried.

To regenerate the insoluble support and add a different protein, step 8 of Example 1 is followed.

EXAMPLE 7

Agarose beads—C-L-Valine Methyl Ester—DCC in 1,4-dioxane activation

The same procedure as in Example 6 was followed, except activation (step 6) was performed by reacting with dioxane. In this method 3 ml. of packed gel was suspended in 9 ml. of 1,4-dioxane containing 0.2 g. dicyclohexylcarbodiimide and 30$\mu$ moles of $^{14}$C-L-Valine methyl ester. The reaction proceeded for 90 minutes at room temperature after which the resin was washed in 2 volumes of dioxane followed by 2 volumes of methanol and later 4 volumes of dioxane.

EXAMPLE 8

Agarose beads—C-L-Valine Methyl Ester—dimethylformamide activation

The same procedure as in Example 6 was followed, except activation (step 6) was performed by reacting with DCC in 50% dimethylformamide in methanol. In this method, 3 ml. packed gel was washed with 50% dimethylformamide in methanol, then suspened in 9 ml. of the same solvent. The reaction was initiated by adding 0.2 g. dicyclohexylcarbodiimide and 30$\mu$ moles of C-L-Valine methyl ester. After 90 minutes the resin was washed with 6 volumes of 50% dimethylformamide in methanol.

Although agarose beads or polystyrene have been described as supports, other conventional supports may be used as explained in the co-pending application above. Thus glass beads dextran or the like are also suitable. Moreover, different length arms between 5 and 15 angstrom units may be used as explained in the co-pending application. Similarly, carboxyl groups, with judicious choice of phenolic or aromatic amino to generate the azo linkages may be substituted with other groups to attach the protein.

The effectiveness of regeneration in the above examples was measured by determining the available binding sites after regeneration. To study the effective reaction time on the quantitative attachment of $^{14}$C-L-Valine Methyl Ester, aliquots were drawn at 20, 40, 70, 90, 120, 140 and 160 minutes from the reaction mixture using dioxane as described above. The resin was washed, dried and assayed for radioactivity. There was no noticeable change after 60 minutes.

The amount of enzyme was measured from the rate of hydrolysis of o-nitrophenyl-$\beta$-D-galactopyranoside by the resin. The matrix was suspended in two volumes of dioxane and to it were added dicyclohexyl carbodiimide and N-hydroxysuccinimide to bring their concentration to 0.1 molar. The reaction was allowed to proceed for 90 minutes and the resins were washed successively with dioxane, methanol and dioxane.

The resins were air dried for 10 minutes to evaporate residual dioxane and then suspended in an equal volume of 0.1 molar potassium phosphate buffer at a pH of 7.0, containing 40 milligrams of lactase per milliliter of packed gel. The reaction was allowed to proceed for 16 hours at 4° C. and then terminated by rendering the reaction mixture 0.2 M with glycine. The product was washed extensively with 0.1 M phosphate buffer at a pH of 7 until all surface absorbed enzyme was eluted. Aliquots of the immobilized enzyme were assayed using o-nitrophenyl-$\beta$-D-galactopyranoside as the substrate.

The soluble and immobilized forms of the enzymes were used to determine the pH optimum for assay and for the apparent Michaelis constant. The kinetic data were analyzed statistically by the method of Wilkinson. Recycling results in a slight decrease in the amount of lactase bound as the number of cycles increases. In the case of the coupling with methyl ester there was no reduction and with *Saccharomyces lactis* lactase only a slight reduction in 5 cycles. The amount of lactase bound decreased from 0.40 mg. to 0.33 in the 5 cycles. The ability was tested by the ability of the column to react with valinemethyl ester in the presence of dicyclohexyl carbodiimide or lactase when the resin was activated with dicyclohexyl carbodiimide and N-hydroxysuccinimide.

As can be understood from the above description, the method and the regenerable matrix of this invention has the advantages of permitting an insoluble matrix to be bound to proteins such as enzymes or for affinity chromatography or other purposes and after the protein has been spent, to have the protein removed and the same insoluble matrix bound to further protein of either the same kind or different kind for further processing.

Although a preferred embodiment has been described with some particularity, many modifications and variations are possible in the embodiment without deviating from the invention. It is therefore to be understood that, within the scope of the appended claims, the invention may be practiced other than as specifically described.

What is claimed is:

1. A process of preparing a solid insoluble carrier for replaceably immobilizing proteins, comprising the steps of:
    coupling to said solid insoluble carrier, chemical arms including diazo linkages within them and a group that forms a bond with functional groups of the proteins; and
    the step of coupling comprising covalently coupling one end of chemical arms to a solid insoluble chemical carrier wherein each coupled arm has a length of between 5 and 15 angstrom units from said one end to the other, each arm has therein between its ends a diazo linkage and each arm has adjacent the diazo linkage a phenolic compound containing a carboxylic acid group or an aromatic compound containing a carboxylic acid group on its other end that forms a covalent bond to an $\alpha$-amino group of the protein remote from the active center of the protein under a predetermined set of chemical conditions.

2. A process according to claim 1 wherein the phenolic compound is N-acetyl-L-tyrosine.

3. A process of preparing and using a solid insoluble carrier for replaceably immobilizing proteins, comprising the steps of:
    coupling to said solid insoluble carrier chemical arms including diazo linkages within them and a group that forms a bond with functional groups of the proteins;
    the step of coupling comprising covalently coupling one end of chemical arms to the solid insoluble carrier wherein each coupled arm has a length of between 5 and 15 angstrom units from said one end to the other and each arm has therein between the ends a diazo linkage and each arm has adjacent the diazo linkage a phenolic compound containing a carboxylic acid group or an aromatic compound containing a carboxylic acid group on its other end that forms a covalent bond to an $\alpha$-amino group of the protein remote from the active center of the protein under a predetermined set of chemical conditions;
    covalently coupling the $\alpha$-amino group of a protein to said carboxylic acid group to immobilize the protein on the carrier
    using said solid carrier with said immobilized protein as a reactor;
    reducing said diazo bond when said proteins are spent to remove said spent protein; and
    forming a new arm with a diazo linkage adapted to receive a new protein.

4. A process according to claim 3 wherein the phenolic compound is N-acetyl-L-tyrosine.

5. A process according to claim 3 in which the step of using said solid carrier with an immobilized protein includes the step of using said solid carrier with lactase attached thereto.

6. A process according to claim 5 in which the step of using said solid carrier with said immobilized protein as a reactor includes the step of using said solid carrier with immobilized *Saccharomyces lactis* lactise.

7. A reactor comprising:
    a solid carrier and protein;
    said solid carrier including a matrix and a spacer arm;
    said spacer arm being between 5 and 15 angstrom units in length and having a diazo group within it and adjacent the diazo group a phenolic compound containing a carboxylic acid group or an aromatic compound containing a carboxylic acid group that is covalently bonded with only one reactive functional group of the protein at the $\alpha$-amino group.

8. A reactor according to claim 7 in which said protein is an enzyme.

9. A reactor according to claim 8 in which said enzyme is *Saccharomyces lactis* lactase.

10. A reactor according to claim 7 in which the phenolic compound is N-acetyl-L-tyrosine.

11. A reactor according to claim 10 in which said protein is an enzyme.

12. A reactor according to claim 10 in which said enzyme is *Saccharomyces lactis* lactase.

* * * * *

UNITED STATES PATENT AND TRADEMARK OFFICE
CERTIFICATE OF CORRECTION

PATENT NO. : 4,279,998
DATED : July 21, 1981
INVENTOR(S) : Khemchand M. Shahani, Frederick Wagner & Arun Kilara It is certified that error appears in the above—identified patent and that said Letters Patent is hereby corrected as shown below:

Equation 1, insert "§" after the first --→-- .

Column 2, line 8, change "regeneratable" to --regenerable--.

Column 2, line 19, change "a" to --an--.

Column 3, line 27, change "(Sepharose)" to --Sepharose)--.

Column 9, line 40, change "Saccharomyces lactis" to --Saccharomyces lactis--.

Column 9, line 40, delete the second occurrence of lactase.

Column 10, line 68, change "example" to --Example--.

Column 12, line 31, change "suspened" to --suspended--.

UNITED STATES PATENT AND TRADEMARK OFFICE
CERTIFICATE OF CORRECTION

PATENT NO. : 4,279,998
DATED : July 21, 1981
INVENTOR(S) : Khemchand M. Shahani, Frederick Wagner & Arun Kilara It is certified that error appears in the above—identified patent and that said Letters Patent is hereby corrected as shown below:

IN THE CLAIMS:

Column 14, line 23, after the word "carrier" insert ";".

Signed and Sealed this

Eleventh Day of May 1982

[SEAL]

Attest:

GERALD J. MOSSINGHOFF

Attesting Officer *Commissioner of Patents and Trademarks*